(12) United States Patent
Hunger et al.

(10) Patent No.: US 11,035,842 B2
(45) Date of Patent: Jun. 15, 2021

(54) NEEDLE-GUIDING DEVICE FOR A DRILLING RESISTANCE MEASUREMENT UNIT, DRILLING RESISTANCE MEASUREMENT UNIT, AND DRILLING RESISTANCE MEASUREMENT METHOD FOR INVESTIGATING THE NATURE OF WOOD

(71) Applicant: IML Instrumenta Mechanik Labor GmbH, Wiesloch (DE)

(72) Inventors: Erich Hunger, Karlsruhe (DE); Sebastian Hunger, Leimen (DE); Fabian Hunger, Leimen (DE)

(73) Assignee: IML Instrumenta Mechanik Labor GmbH, Wiesloch (DE)

( * ) Notice: Subject to any disclaimer, the term of this patent is extended or adjusted under 35 U.S.C. 154(b) by 421 days.

(21) Appl. No.: 16/067,896

(22) PCT Filed: Sep. 22, 2017

(86) PCT No.: PCT/EP2017/001132
§ 371 (c)(1),
(2) Date: Jul. 3, 2018

(87) PCT Pub. No.: WO2018/065086
PCT Pub. Date: Apr. 12, 2018

(65) Prior Publication Data
US 2020/0264159 A1  Aug. 20, 2020

(30) Foreign Application Priority Data
Oct. 4, 2016  (DE) .................... 10 2016 011 776.1

(51) Int. Cl.
*G01N 33/46* (2006.01)
*B23B 49/00* (2006.01)
*G01N 3/40* (2006.01)

(52) U.S. Cl.
CPC ............. *G01N 33/46* (2013.01); *B23B 49/00* (2013.01); *G01N 3/40* (2013.01)

(58) Field of Classification Search
CPC ...................................................... G01N 33/46
(Continued)

(56) References Cited

U.S. PATENT DOCUMENTS

| 6,290,437 B1 | 9/2001 | Mattheck et al. |
| 2013/0104634 A1 | 5/2013 | Hunger et al. |

(Continued)

FOREIGN PATENT DOCUMENTS

| AU | 593703 | 2/1990 |
| DE | 41 22 494 | 3/1992 |

(Continued)

*Primary Examiner* — Walter L Lindsay, Jr.
*Assistant Examiner* — Philipmarcus T Fadul
(74) *Attorney, Agent, or Firm* — Gudrun E. Huckett

(57) ABSTRACT

The present invention relates to a needle-guiding device (2) for a specified drilling resistance measurement unit, a drilling resistance measurement unit itself for investigating the nature of wood, and to a method for investigating the nature of wood. The needle-guiding device (2) for the drilling resistance measurement unit is designed to guide the drill needle (1) and to be operatively coupled to a drive of the drilling resistance measurement unit. The needle-guiding device (2) has a supporting device and a needle holder (4). The needle holder (4) has a drill chuck which is designed to receive the specified drill needle (1), and the supporting device extends in the longitudinal direction of the specified drill needle (1). According to the invention, the supporting device comprises at least one scissor-type extending grid device (8) having a scissor-type extending grid (8') consisting of bars (81) or has a drive device having two interacting force transmission elements which are arranged parallel next to each other.

18 Claims, 4 Drawing Sheets

(58) Field of Classification Search
USPC .............................................................. 73/81
See application file for complete search history.

(56) References Cited

U.S. PATENT DOCUMENTS

| | | | | |
|---|---|---|---|---|
| 2015/0183073 A1* | 7/2015 | Rinn | ..................... | E21B 49/003 |
| | | | | 408/2 |
| 2015/0233806 A1* | 8/2015 | More | ....................... | G01N 3/40 |
| | | | | 73/85 |
| 2016/0221087 A1 | 8/2016 | Hunger et al. | | |
| 2017/0184480 A1 | 6/2017 | Hunger et al. | | |

FOREIGN PATENT DOCUMENTS

| | | |
|---|---|---|
| DE | 297 07 307 | 1/1998 |
| DE | 100 31 395 | 4/2001 |
| DE | 10 2010 018 249 | 10/2011 |
| DE | 10 2013 001 711 | 8/2014 |
| DE | 10 2013 015 131 | 1/2015 |
| DE | 10 2014 227 029 | 7/2015 |
| DE | 10 2014 013 412 | 3/2016 |
| GB | 1 103 810 | 2/1968 |
| JP | 2003103409 | 4/2003 |
| WO | 2012/167777 | 12/2012 |

\* cited by examiner

NEEDLE-GUIDING DEVICE FOR A DRILLING RESISTANCE MEASUREMENT UNIT, DRILLING RESISTANCE MEASUREMENT UNIT, AND DRILLING RESISTANCE MEASUREMENT METHOD FOR INVESTIGATING THE NATURE OF WOOD

BACKGROUND OF THE INVENTION

The invention concerns a needle-guiding device, a drilling resistance measurement unit with a needle-guiding device according to the invention, and a method for investigating the nature of wood by means of the drilling resistance measurement unit including the needle-guiding device.

The prior art discloses drilling resistance measurements and properties investigations in which trees, wood poles or wood in another form are examined in regard to defects or decay. For these investigations, drilling resistance measurement units are employed. Such a drilling resistance measurement unit is known, for example, from DE 10 2013 001 711.

In these drilling resistance measurement units, thin drilling needles are employed for the monitored drilling resistance measurement process. It is known to support these drilling needles during the drilling process against a movements transverse to the drilling direction. For example, DE 100 31 395 discloses a special cup telescope that guides the drilling needle in the cup bottom and is retractable in that the smaller cups are moved into the next larger one.

A device for testing wood is disclosed also in DE 41 22 494. This device also comprises cylindrical telescoping sleeves in which the drilling needle is centrally guided.

DE 10 2010 018 249 A1 discloses a manual testing device for investigating the nature of wood with a guiding device for guided insertion of the drilling needle into the object to be examined. The guiding device is a telescope tube that comprises a shorter inner tube section which is axially slidably arranged in a longer outer tube section and which, at its outer circumference, comprises a measurement scale arranged in longitudinal direction. The telescoping tube is non-rotatingly placed by means of the inner tube section onto the drive device. The inner and the outer tube sections comprise guide means for central-axial guiding of the drilling needle which extends central-axially from the drill chuck through the inner tube section and through the outer tube section. In this way, upon pushing the inner tube section into the outer tube section, the drilling needle, guided by means of the guide means, can be driven into the object to be examined.

DE 10 2013 015 131 B3 discloses a drill chuck and a drilling needle drill chuck assembly with a clamping device for detachably receiving the drilling needle. Moreover, the drill chuck has a front cover with an opening for the drilling needle wherein in the opening a drilling needle guide sleeve of a device for guiding the drilling needle is rotatably supported so that the drilling needle guided in the drilling needle-guiding device upon coupling of the drill chuck with the drive device is positioned co-centrally with a motor output shaft of the drive device.

A further device for drilling resistance measurement in a material to be examined is disclosed in DE 10 2014 227 029 A1 which, for guiding the drilling needle, comprises a plurality of U-shaped guide elements, with legs of different length and a base area connecting the two legs, that are slidable along a drilling axis. In each one of the longer legs a passage for the drilling tool for guiding the drilling tool is formed.

WO 2012/167777 A1 describes a needle changing cartridge for a drilling resistance measurement unit which comprises a guiding device for a drilling needle which is embodied as a telescope tube with a plurality of telescoping tube sections. The plurality of telescoping tube sections extends between a working end where a holder for rotationally fixed holding of the drilling needle is arranged and a docking end where a docking device for coupling the telescope tube with a drive device of the drilling measurement unit is arranged. The docking device comprises a coupling device for torque transmission from the drive device of the drilling needle resistance measurement unit to the telescope tube and a gear device for converting the rotary movement of the drive device of the drilling measurement unit into a linear movement of the telescope tube.

GB 1,103,810 A describes a soil drilling device for use in installing posts. The soil drilling device can be mounted on a frame which is attached to a self-propelled vehicle. A double-scissor extension device is connected rotatably at one end with a reduction gear drive and at the other end, by means of a counter bearing, connected with a shaft which can be brought into engagement with the drive and in this way can be rotated and which is connected with a drill bit.

When using the telescoping sleeves, the sequentially arranged telescoping sleeves or cups have a great contact surface relative to the respective next telescoping sleeve. Friction is generated by movement of the telescoping sleeves—these friction forces must be overcome. The great friction value has an effect on the feed measurement.

Based on this prior art, it is the object of the present invention to provide an improved needle-guiding device.

SUMMARY OF THE INVENTION

This object is solved by a needle-guiding device characterized in that the support device comprises at least one scissor-type extension arm device with a scissor-type extension arm of stays, or characterized in that the support device is a drive device that comprises two interacting force transmitting elements that are arranged parallel adjacent to each other.

The further object of providing an improved drilling resistance measurement unit with an improved needle guiding action is solved by a drilling resistance measurement unit comprising a needle-guiding device characterized in that the support device comprises at least one scissor-type extension arm device with a scissor-type extension arm of stays, or comprising a needle guiding device characterized in that the support device is a drive device that comprises two interacting force transmitting elements that are arranged parallel adjacent to each other.

The object of providing an improved method for drilling resistance measurement is solved by the method for investigating the nature of wood by use of a needle-guiding device characterized in that the support device comprises at least one scissor-type extension arm device with a scissor-type extension arm of stays, the method comprising the steps:
 providing a drilling resistance measurement unit with the needle-guiding device and clamped drilling needle,
 transferring the scissor-type extension arm of stays of the scissor-type extension arm device of the support device of the drilling needle of the needle-guiding device into an extended state, then placing the needle-guiding device with the drilling needle against an object of wood to be examined, then inserting the drilling needle into the object of wood and, in doing so, simultaneously transferring the scissor-type extension arm into the folded state.

The object of providing an improved method for drilling resistance measurement is solved by the method for investigating the nature of wood by using a needle-guiding device characterized in that the support device is a drive device that comprises two interacting force transmitting elements that are arranged parallel adjacent to each other, the method comprising the steps:

providing a drilling resistance measurement unit with the needle-guiding device and clamped drilling needle and guiding the drilling needle in the support device, which as a drive device comprises a chain drive that comprises two chains as force transmitting elements, or in the support device which as a drive device comprises a belt drive that comprises two toothed belts as force transmitting elements, positioning the needle holder in the rear position at the drive device, placing the needle-guiding device with the drilling needle against an object of wood to be examined, then inserting the drilling needle into the object of wood, and in doing so simultaneously transferring the needle holder into the forward position.

Preferred embodiments of the devices or of the method are disclosed in the dependent claims.

A first embodiment of the needle-guiding device according to the invention for a specified drilling resistance measurement unit is configured to guide a specified drilling needle and to be operatively coupled to a drive of the drilling resistance measurement unit. The needle-guiding device comprises a support device, which extends in longitudinal direction of the specified drilling needle, and a needle holder with a drill chuck in which the drilling needle is received and clamped.

An "operative coupling" of the needle-guiding device to a drilling resistance measurement unit means that a force-transmitting connection from the drive or drives of the drilling resistance measurement unit to the movable parts of the needle-guiding device and a data transmission for transmitting determined feed and resistance data are produced, insofar as this is required.

"Specified drilling needle" and "specified drilling resistance measurement unit" means, of course, that this needle as well as the machine which provides the drive action must be matched to each other and to the wood object to be tested; and, of course, also the support device for the drilling needle must be dimensioned in such a way that it is suitable to support, on the one hand, the length of the needle and to permit, on the other hand, that the needle can be optimally utilized.

According to a first embodiment in accordance with the invention, the support device is a scissor-type extension arm device that comprises a scissor-type extension arm of stays.

The scissor-type extension arm can be transferred from an extended to a folded state and defines a plane E. For transferring into a folded and an extended state, scissor linkages are provided as is known in general for scissor-type extension arms. Two stays are crossing each other, respectively, and are connected by means of a joint. However, according to the invention, each joint ends in a support structure which extends away normal relative to the plane E defined by the scissor-type extension arm. In this context, the component which comprises the joint function and the support function is referred to as support structure with joint. Each support structure has a passage that serves as a receptacle for the drilling needle. The passages of all support structures for the drilling needle are aligned with each other and with an opening of the needle holder.

By guiding the drilling needle in the passages, the needle can run almost freely and can rotate with low friction. In order to reduce the friction further, it is possible to design the complete component, or at least the passages, with special shapes and materials so that the friction is further reduced. For example, the passage can be provided with a lining, for example, of Teflon.

The needle is supported by the scissor-type extension arm at regular intervals so that even under load it is protected from breakage because between the support points a bulging deformation of the needle is possible so that it can give way.

The stays of the scissor-type extension arm, aside from the joints at the crossing points, are also connected at the ends of the stays with respective next crossing stay pairs so that friction will occur only at these connecting points. In this context, the joints can be optimized with regard to friction so that a smaller friction surface is produced and/or this friction surface is provided with a material that ensures smaller friction forces. Since the disturbance parameter friction resistance has an effect on the drilling resistance measurement which detects the feed resistance of the needle, the drilling resistance measurement with the device according to the invention is more exact than with devices of the prior art because these disturbance parameters have been minimized. In short, the contact surface of the points of intersection is significantly reduced in comparison to the telescoping sleeves, and the smaller the contact surface the more reduced the friction that occurs.

The scissor-type extension arm of the needle-guiding device comprises in the extended state a length that is selected such that the specified drilling needle in a position received in the drill chuck does not extend past the scissor-type extension arm. In the folded state, the scissor-type extension arm has a length that is selected such that at least half of the specified drilling needle projects from the scissor-type extension arm.

In use, in which the drilling needle of the drilling resistance measurement unit is driven into a tree or into another wood object (e.g. line pole), the drilling needle-guiding device guides the drilling needle which is running in the passages of the support structure. In this context, the rear end of the drilling needle is fastened in a chuck of the needle holder or of the drilling resistance measuring unit and the leading end is contacting the wood. During the drilling process, the scissor-type extension arm is folded step-by-step and the part of the drilling needle which is projecting from the scissor-type extension arm is driven into the wood. The scissor-type extension arm is contacting the wood during the entire process.

When folding the scissor-type extension arm, the angle of the stays relative to the drilling needle becomes greater and the scissor-type extension arm thus becomes wider. All passages move uniformly toward each other so that the ratio of the spacings of the passages and thus of the guiding locations always remains the same.

Advantageously, for a plurality of or for all of the support structures, a shaped body is provided at least at one end, wherein in the folded state of the scissor-type extension arm the shaped bodies which are lying on the same side of the plane E are resting flush against each other so that the scissor-type extension arm in the folded state does not cant. The shaped bodies are preferably sliding blocks. They are designed such that they cannot turn out of position, guide linearly, and are extremely compact in the contracted state. Suitably, the sliding blocks which are arranged in pairs are mounted at the top and bottom, rotated by 180° relative to each other, respectively.

A support structure can be fastened with the section which comprises the passage for the drilling needle immediately at one of the stays which form a cross of the scissor-type extension arm so that the section of the support structure that is provided with the joint is positioned inside the stays or the stays enclose the joint section.

The support structure with joint can advantageously be of a two-part or multi-part configuration so that all parts—like those of the scissor-type extension arm—can be manufactured and mounted in a simple way.

For example, a first thread-constituting section of the support structure can be a sleeve to which one of the two stays crossing each other is connected and a second thread-constituting section is a pin with which the second stay is connected, wherein the pin is rotatably engaging the sleeve.

In practice: when, for example, a first section of the support structure is formed as a pin in order to form a lower section of the thread, the pin in the mounted state can then be pushed through the lower stay and the stay positioned above in order to be received by screwing action in a sleeve which forms the next (second) thread-constituting section which extends past the upper stay and which extends as one piece, or by connection, into the section with the passage.

When this concept is further developed, the section with the passage at the other end (facing away from the thread side) can again end in a threaded pin which is received by a shaped body that has an inner thread in order to be received thereby in the section with the passage.

In yet another embodiment, the first section of the support structure embodied as a pin, in order to form a lower section of the thread, can also be provided at its thread-remote side with another thread or can be embodied as a sleeve, can be received by a shaped body which has an inner thread, or receive a shaped body accordingly.

The configuration of the components with corresponding threads is also reversible, in principle.

Moreover, the components can also be connected in a different way to each other; for example, by compression, locking action or in another way known to a person of skill in the art.

Respecting "lower" and "upper": "upper side" is the side of the joint or of the support structure which is facing upwardly in case of ground-parallel orientation of the plane E of the scissor-type extension arm; "lower side" is facing downwardly in this case. This concept of top and bottom applies in general and also when the device is used in any slanted position.

The lower end of the support structure can end at the same time also with the joint section so that no free end projects from the scissor-type extension arm.

In yet another embodiment, it is possible that the support structure is connected directly with the scissor-type extension arm in that it is screwed thereto or riveted thereto.

In a needle-guiding device, the scissor-type extension arm device can be in operative connection with a feed drive of a specified drilling resistance measurement unit so that the scissor-type extension arm is transferable from the folded state into the extended state by the feed drive. For this purpose, the feed drive can be connected to the ends of the stays which are positioned at the edge and are oriented toward the drilling resistance measurement unit. In this way, the ends of these stays can be pushed apart and, in this way, by means of the joint connections, the scissor-type extension arm can be folded or the ends are pushed together and the scissor-type extension arm extended in this way.

In yet another embodiment, the scissor-type extension arm device comprises two scissor-type extension arms whose planes E in the extended state are positioned parallel to each other. In this context, one joint of one scissor-type extension arm is connected by means of a common support structure with the corresponding joint of the other scissor-type extension arm. The scissor-type extension arms are preferably arranged such that the passages of the support structure of the joints are positioned between the two scissor-type extension arms. The two scissor-type extension arms of such an arrangement should have the same shape so that the joint points in a projection onto one of the planes E are congruent and the stays thus also have the same length and, when folded, move at the same speed. The support structure of the joints is then oriented normal to the two planes E.

By arrangement of two scissor-type extension arms a higher bending stiffness can be achieved because the area moment of inertia is enlarged since the scissor-type extension arms are arranged at both sides of the drilling needle and can be spaced farther away from the drilling needle.

In an alternative embodiment of the needle-guiding device, the support device is a drive device which comprises two parallel adjacently arranged interacting force transmitting elements.

The drive device can be embodied by a chain drive or by a belt drive. In this context, the chain drive comprises two chains as force transmitting elements, the belt drive two toothed belts.

In an embodiment, the two chains or the two toothed belts are tensioned at one end about a pinion and at the other end about a drive pinion. The drive pinions are configured to be driven by a feed drive of the specified drilling resistance measurement unit. The needle holder is fastened to the drive device and is transferred by the drive device from a rear position into forward position. In the rear position, the needle holder is positioned at the end of the drive device which is positioned at the drilling resistance measuring unit in a state of use. In the forward position, the needle holder is positioned at the other end of the drive device.

The force transmitting elements comprise guide elements, and a respective guide element of one force transmitting element is in operative connection with a guide element of the other force transmitting element. Both guide elements together form an enclosure for the specified drilling needle.

The drilling needle is positioned between the two force transmitting elements which are arranged on opposite sides of the drilling needle. The drilling needle is pushed with the needle holder in which it is clamped from the rear position into the forward position. In this context, the drilling needle, which in the rear position is completely positioned between the force transmitting elements and is supported by all guide elements arranged between the force transmitting elements, is gradually moved into the forward position in which it is projecting far past the drive device. During the movement, the guide elements which are in operative connection become sequentially detached from each other when they are moved away from each other at the location of the pinion. The drilling needle is thus enclosed and guided by fewer and fewer guide elements. In this context, the force transmitting elements move together with the drilling needle so that no relative movement between the drilling needle and the force transmitting elements exists. Therefore, no friction in the longitudinal direction of the drilling needle is generated. In use, the drilling needle is driven into the wood by this movement.

The movement is achieved by a synchronous drive action of the drive pinions wherein the rotational directions are opposite. The force transmitting elements are driven by the drive pinions and move the needle holder.

In yet another embodiment, the two chains are formed of chain members which have bolts and links. The receptacle of the drilling needle is formed by the bolts of the chain members. In this context, the bolts can have an inward curvature which corresponds to a negative shape of the drilling needle. The drilling needle is then supported respectively by the bolts in the direction of the chain.

The two chains can be extending adjacent to each other in such a way that the links of the chain members are meshing. This means that the chain members of the two chains are arranged staggered relative to each other so that a concave portion of the chain member or of the link receives a convex portion of the chain member of the other chain. A relative movement of the two chains is then no longer possible. Both chains must be moved at the same speed.

According to another possible embodiment, the toothed belts comprise hooks at their side without teeth. The hooks of one toothed belt engage the hooks of the other toothed belt. By engagement of the hooks with each other, a relative movement of the two toothed belts relative to each other is prevented here also.

The hooks comprise each a cutout which is facing away from the belt. These cutouts overlap in the engagement position and form a round passage as an enclosure for the specified drilling needle. The drilling needle is thus guided at one side by the cutout of the hook of one belt and at the other side by the cutout of the hook of the other belt.

The drilling resistance measurement unit according to the invention for investigating the nature of wood comprises a needle-guiding device in one of the listed embodiments.

The drilling resistance measurement unit can furthermore comprise a feed drive. This feed drive can be coupled with the drive pinion of a drive device in a force-transmitting way and/or can be connected such with the scissor-type extension arm in a force-transmitting way that the scissor-type extension arm by means of the feed drive is transferred from the folded state into the extended state.

A method according to the invention for investigating the nature of wood is realized by use of a needle-guiding device according to the invention with a scissor-type extension arm device and comprises the following steps:

providing a drilling resistance measurement unit with a needle-guiding device and clamped drilling needle, transferring the scissor-type extension arm of stays of the scissor-type extension arm device of the support device of the drilling needle of the needle-guiding device into an extended state, then placing the needle-guiding device with the drilling needle against an object of wood to be examined, then inserting the drilling needle into the object of wood and, in doing so, simultaneously transferring the scissor-type extension arm into the folded state.

A further method according to the invention for investigating the nature of wood is realized by use of a needle-guiding device according to the invention with a drive device and comprises the following steps:

providing a drilling needle resistance measurement unit with the needle-guiding device and clamped drilling needle and guiding the drilling needle in the support device, which comprises as a drive device a chain drive which comprises two chains as force transmitting elements, or in the support device which comprises as a drive device a belt drive which comprises two toothed belts as force transmitting elements, positioning the needle holder in the rear position at the drive device, placing the needle-guiding device with the drilling needle against an object of wood to be examined, then inserting the drilling needle into the object of wood, and, in doing so, simultaneously transferring the needle holder into the forward position.

Further embodiments as well as some of the advantages which are associated with these and further embodiments will become clear and well understood by means of the following detailed description with reference to the accompanying figures. Objects or parts thereof which are substantially identical or similar can be provided with the same reference characters. The figures are only schematic illustration of an embodiment of the invention.

BRIEF DESCRIPTION OF THE DRAWINGS

It is shown in.

DESCRIPTION OF PREFERRED EMBODIMENTS

Figure 1:
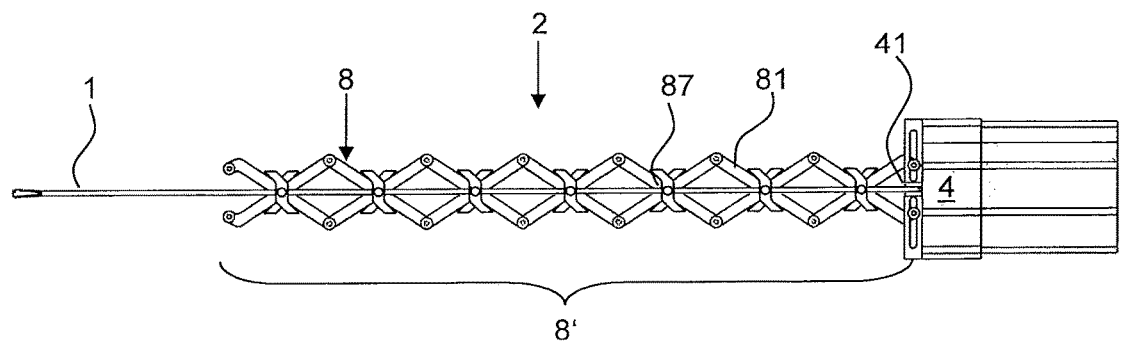
FIG. 1 a plan view of a needle-guiding device with a scissor-type extension arm device with claimed drilling needle, FIG. 2 a perspective view of the needle-guiding device of FIG. 1, FIG. 3 a perspective front view of the leading part of the scissor-type extension arm device of FIG. 1, FIG. 4 a plan view of a paired sliding block arrangement FIG. 5 a plan view of a needle-guiding device with a belt drive with clamped drilling needle, FIG. 6 a perspective front view of the forward part of the belt drive of FIG. 4, FIG. 7 a plan view of a needle-guiding device with a chain drive with clamped drilling needle, FIG. 8 a perspective front view of the forward part of the chain drive of FIG. 6.
Figure 5:
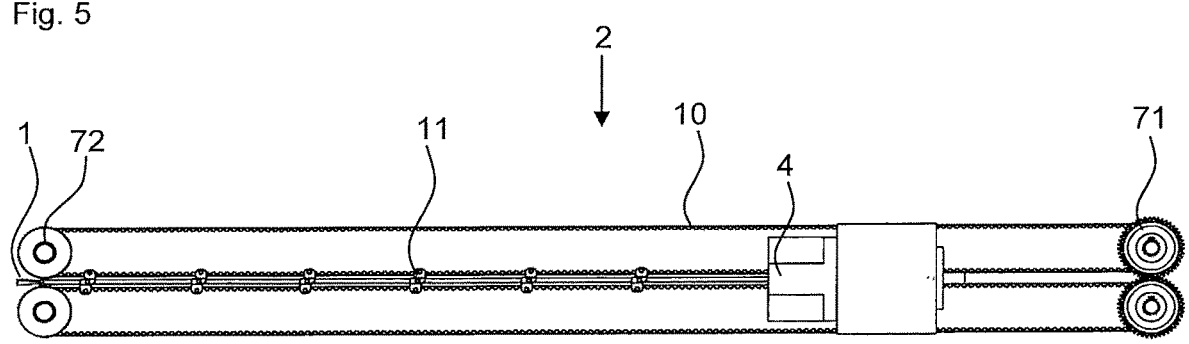
Figure 7:
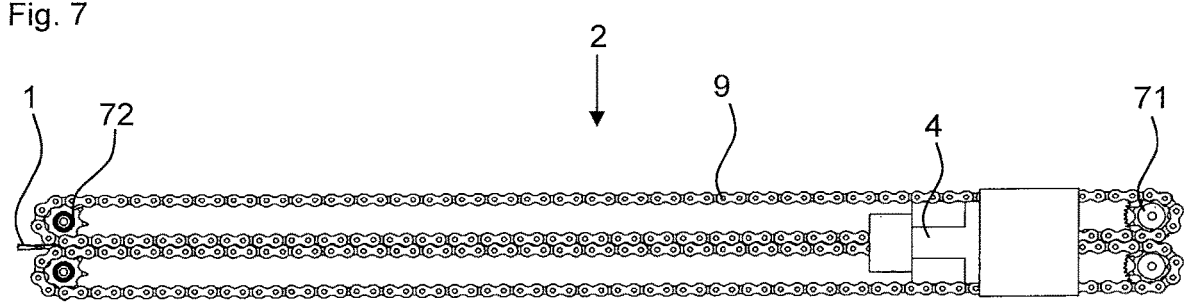

The device according to the invention relates to a needle-guiding device 2 which is illustrated in several embodiments in FIGS. 1, 5, and 7.

Figure 2:
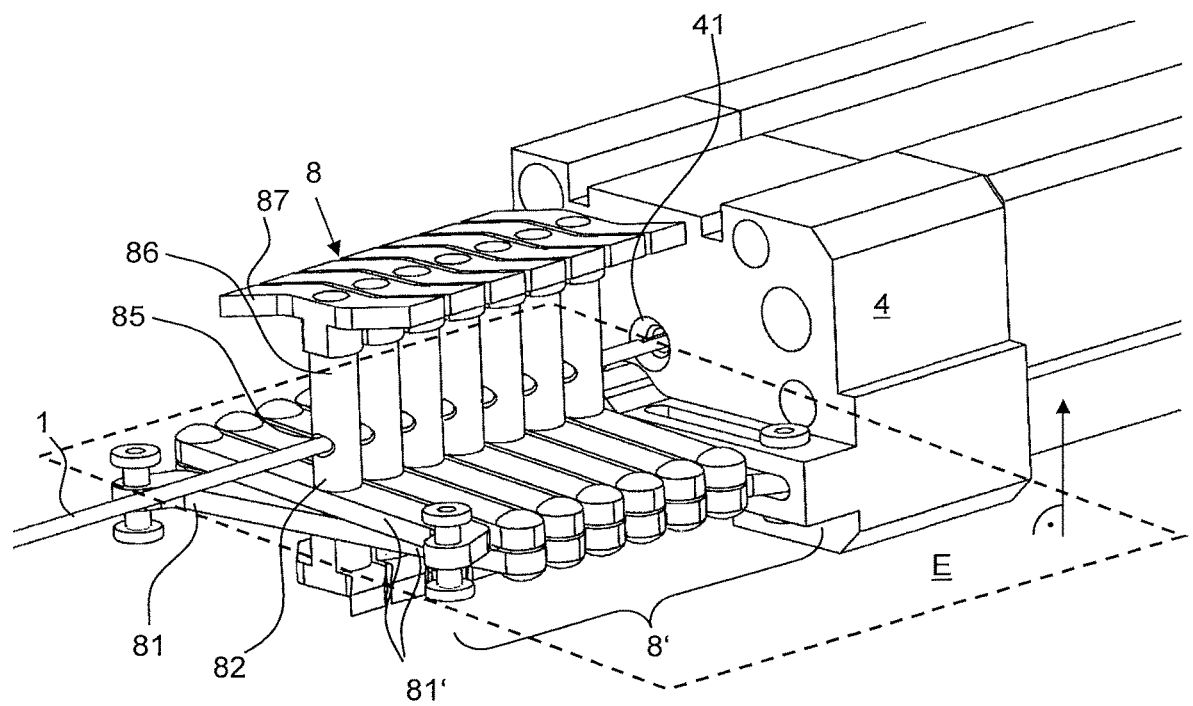
Figure 3:
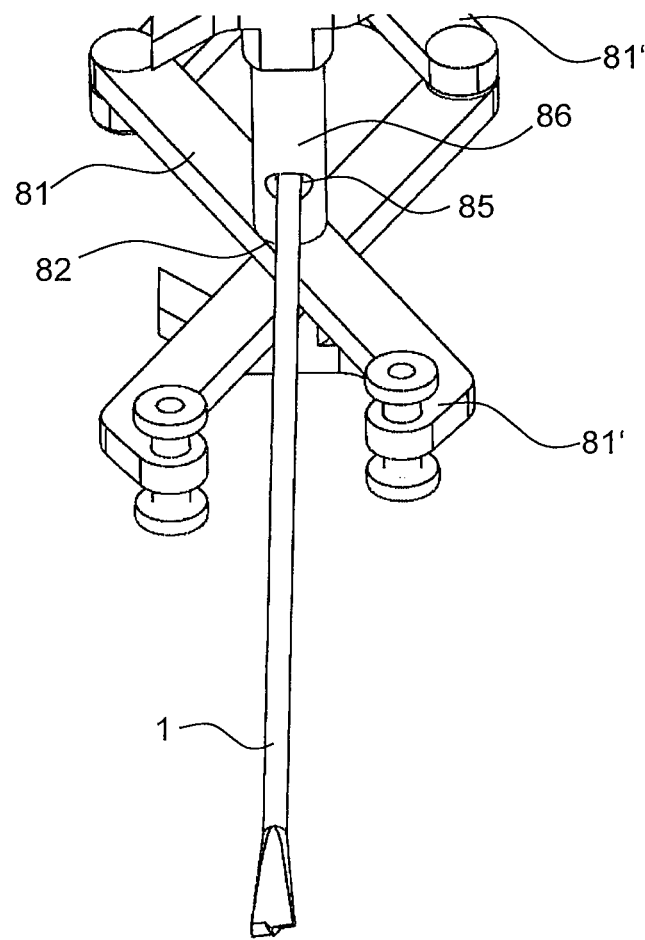

FIGS. 1 to 3 show a needle-guiding device 2 with a scissor-type extension arm device 8 in which the drilling needle 1 is clamped. The scissor-type extension arm device 8 has a scissor-type extension arm 8' which extends in longitudinal direction of the drilling needle 1. The scissor-type extension arm 8' is comprised of stays 81, wherein two crossing stays 81 at their center are connected by a joint 82 that forms a section of the support structure 86 which is extending normal relative to the plane E which is defined by the scissor-type extension arm 8'; see FIG. 2. A passage 85 in which the drilling needle 1 is received is provided in the support structure 86. For this purpose, the passages 85 of the support structures 86 are all aligned such that they are aligned with each other and with the opening 41 of the needle holder 4. FIG. 2 shows also the opening 41 of the needle holder 4 in which the drilling needle 1 is inserted. The drilling needle 1 is secured in the needle holder 4 by a drill chuck.

Figure 4:
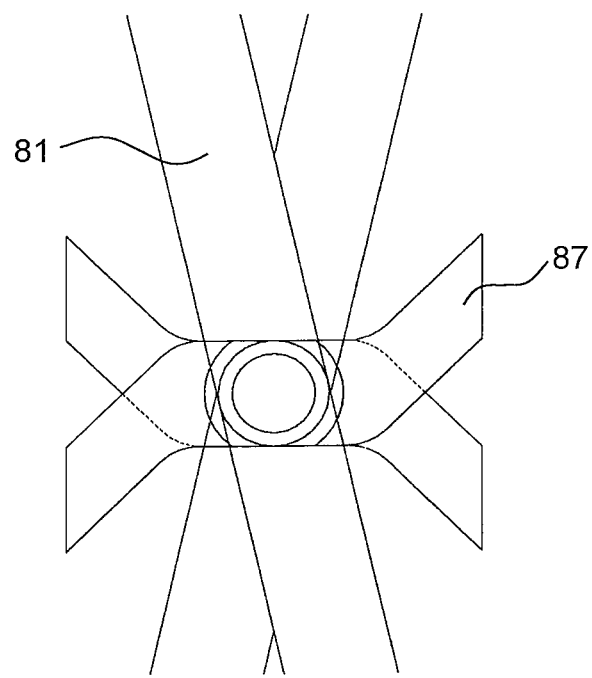

FIG. 2 shows also that the ends 81' of the stays 81 of the scissor-type extension arm 8' are connected pivotably with the ends 81' of the closest stays 81. The ends 81' of the stays 81 which from the end of the scissor-type extension arm 8' at the needle holder 4 are attached to the needle holder 4. For this purpose, the ends 81' of a pair of stays of two associated stays 81 are connected with pins which are guided in slotted holes so that the ends 81' of the stays 81 can only move in one dimension toward each other and away from each other. In this way, the scissor-type extension arm 8' can be folded and extended. FIG. 2 shows the scissor-type extension arm 8' in folded state. The shaped bodies 87 which are present at the free upper ends of the support structures 86 and also below the plane E at the lower sections of the support structures 86, see also FIG. 4 which shows a paired arrangement of two sliding blocks, are arranged flush against each other. In FIG. 1 in which the scissor-type extension arm 8' is extended, the shaped bodies 87 are spaced apart from each other. The shaped bodies 87, which are preferably sliding blocks 87, are designed such that they cannot turn out of position, guide linearly, and are extremely compact in the folded state. In this context it is important that the sliding blocks 87 which are arranged in pairs and are mounted at top and bottom rotated relative to each other by 180°, respectively, as shown in FIG. 4.

FIG. 3 shows only a detail of the scissor-type extension arm device 8 with the leading two stays 81 and a central joint 82 with support structure 86 in which the drilling needle 1 is extending through the passage 85. FIG. 3 shows the scissor-type extension arm 8' in almost completely extended state. Only a small portion of the drilling needle 1 projects past the scissor-type extension arm 8'. When extending and folding the scissor-type extension arm 8', the number of passages 85 in which the drilling needle 1 is guided remains the same. The spacings are uniformly enlarged or made smaller. In the illustrated variant, the spacings between the passages 85 are always of the same size. However, variants are also possible in which the spacings can be different. But even then, the ratio of the spacings always remains of the same size during the folding movement.

Further embodiments in which the support structures 86 with joints 82 are formed of a multi-part configuration and can be screwed together by a thread connection are not illustrated in the Figures.

Also not shown in the Figures is an embodiment in which the scissor-type extension arm device 8 comprises two scissor-type extension arms 8' and the drilling needle 1 is guided between both scissor-type extension arms 8'.

Figure 6:
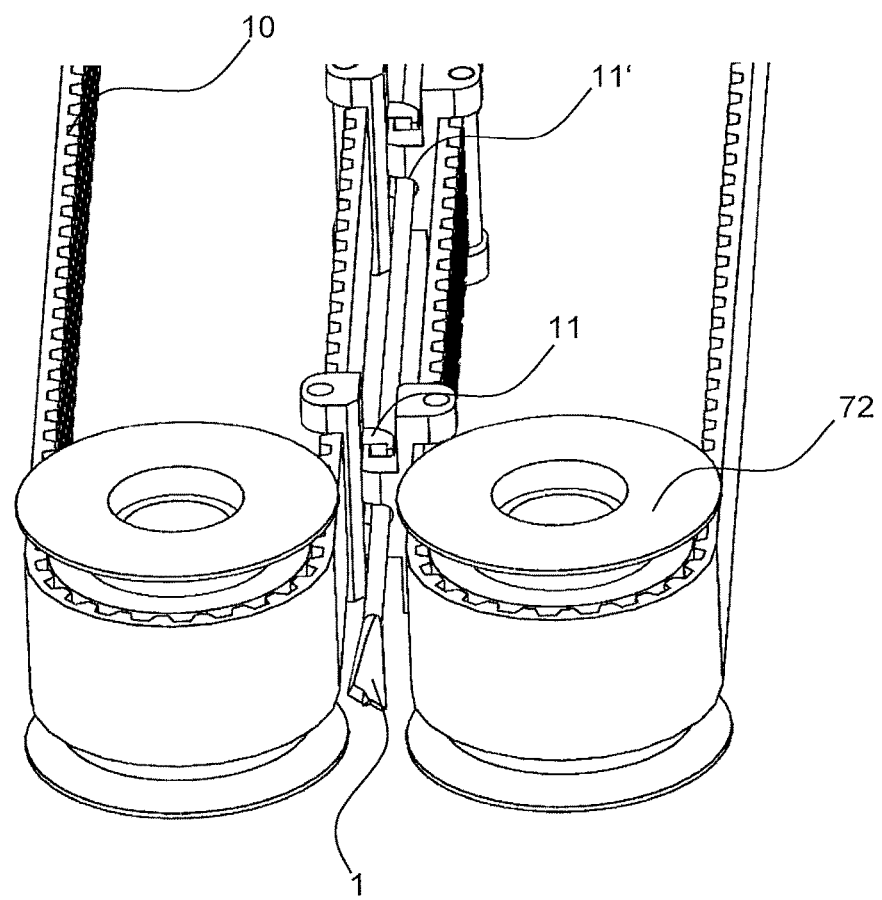

FIGS. 5 and 6 show a needle-guiding device 2 with a belt drive in which the needle holder 4 is moved by the toothed belts 10. The toothed belts 10 are tensioned about a pinion 72 and a drive pinion 71 and are driven by the drive pinion 71. FIG. 5 shows the extension of the toothed belts which are extending parallel to each other at the side facing each other. The drilling needle 1 extends between the two toothed belts 10. For guiding the drilling needle 1, at the side without teeth of the toothed belt 10, hooks 11 are attached which are provided respectively with a cutout 11' open toward the drilling needle 1. At the closed end, this cutout 11' is of a semi-circular shape so that the drilling needle 1 is supported relative to one side in this cutout 11'. Between the two toothed belts 10, the two cutouts 11' of the hooks 11 of the two toothed belts 10 overlap so that, passing through the two cutouts 11', a round passage for the drilling needle 1 remains. The drilling needle is extending through the passages of all hook pairs. This is shown in FIG. 6 in which a detail of the belt drive is illustrated and in which the leading two hook pairs can be seen.

FIG. 6 also shows that two hooks 11 mesh with each other, respectively. This serves the purpose that this connection prevents sliding of the two toothed belts 11 relative to each other and thus a relative movement relative to each other.

In the feed movement of the drilling needle 1, the toothed belts 11 and the drilling needle 1 are moved together. Therefore, no relative movement in the longitudinal direction of the drilling needle 1 between the drilling needle 1 and the needle-guiding device 2 occurs. Therefore, also no friction is produced. Friction occurs only at the cutouts 11' in which the drilling needle is guided because the drilling needle 1 rotates.

Figure 8:
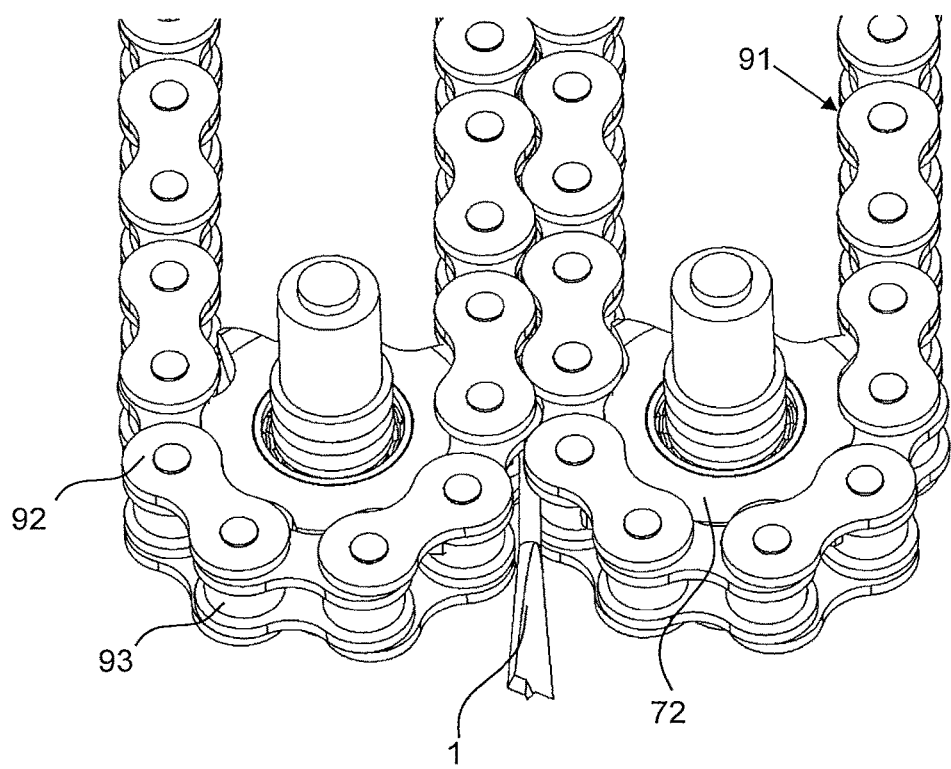

FIGS. 7 and 8 show a needle-guiding device 2 with a chain drive in which the needle holder 4 is moved by chains 9. The chain is constructed of individual chain members 91 which are comprised of bolts 93 and links 92. Two respective links 92 of a chain member 91 are connected pivotably with the two links of the next chain member 91 by a bolt 93. In this way, the chain 9 can adapt to round shapes.

FIG. 7 shows the arrangement of the chain 9 that, like the toothed belt 10, extends about a pinion 72 and a drive pinion 71. Drive pinion 71 and pinion 72 are adapted for this purpose to the chain 9 so that the teeth of the pinion 72 or of the drive pinion 71 can engage into the chain members.

FIG. 8 shows that the drilling needle 1 extends between the adjacently extending chain sections and is supported at the bolts 93 of the chain members 91. Not shown in the Figures is that the bolts 93 can be specially shaped for guiding the drilling needle 1.

In FIGS. 7 and 8 it is also shown that the chains 9 extend adjacent to each other so that the chain members 91 engage each other. For this purpose, the chains 9 are arranged so as to be staggered relative to each other by half a chain member 91. The convex round portion of the link 92 about the bolt 93 is positioned in a concave section of the link 92 between the bolts 93. This position of the chain members 91 relative to each other prevents a relative movement of the two chains 9 relative to each other and a synchronous movement of the chains 9 is ensured.

What is claimed is:

1. A needle-guiding device for a specified drilling resistance measurement unit that is configured to guide a specified drilling needle and configured to be operatively coupled with a drive of the drilling resistance measurement unit, the needle-guiding device comprising:

a needle holder comprising a drill chuck configured to receive the specified drilling needle;

a support device arranged in front of the needle holder and extending in a longitudinal direction of the specified drilling needle, the support device comprising at least one scissor-type extension arm device comprising a first scissor-type extension arm comprised of first stays;

wherein the first scissor-type extension arm defines a plane and is configured to be transferred into a folded state and into an extended state parallel to the plane, wherein the first stays are arranged in sets of two of the first stays, respectively, wherein the two first stays of the sets are crossing each other and are connected to each other pivotably by a support structure comprising a joint, wherein the support structures extend away normal relative to the plane, wherein the support structures each comprise a passage as a receptacle for the specified drilling needle and the passages of all of the support structures are aligned with each other and with an opening of the needle holder.

2. The needle-guiding device according to claim 1, wherein the specified drilling needle has a needle length, wherein the first scissor-type extension arm in the extended state has a first length that is selected such that the specified drilling needle when received in the drill chuck does not project past the first scissor-type extension arm, and wherein the first scissor-type extension arm in the folded state has a second length that is selected such that the specified drilling needle at least with half of the needle length projects past the first scissor-type extension arm.

3. The needle-guiding device according to claim 1, further comprising shaped bodies that are connected to at least one end of at least a plurality of the support structures, respectively, wherein in the folded state of the first scissor-type extension arm the shaped bodies that are positioned on one side of the plane are resting flush against each other.

4. The needle-guiding device according to claim 1, wherein the support structures each have a first section comprising the passage and a second section comprising the joint, wherein the first section is fastened immediately on one of the two first stays of the sets, respectively, and the second section is positioned inside the two first stays of the sets.

5. The needle-guiding device according to claim 1, wherein the support structures each comprise at least two sections connectable to each other by screwing and include a first thread-constituting section and a second thread-constituting section configured to be screwed together.

6. The needle-guiding device according to claim 5, wherein the first thread-constituting section is a sleeve and the second thread-constituting section is a pin, wherein the sleeve is connected to one of the two first stays of the sets crossing each other and the pin is connected to the other of the two first stays of the sets, wherein the pin is rotatably engaging the sleeve.

7. The needle-guiding device according to claim 1, wherein the at least one scissor-type extension arm device is configured to be connected operatively to a feed drive of the specified drilling resistance measurement unit, wherein the first scissor-type extension arm is configured to be transferred by the feed drive from the folded state into the extended state.

8. A drilling resistance measurement unit for investigating the nature of wood, the drilling resistance measurement unit comprising a needle-guiding device according to claim 1.

9. The drilling resistance measuring unit according to claim 8, the drilling resistance measurement unit comprising a feed drive that is configured to transfer the first scissor-type extension arm from a folded state into an extended state.

10. A needle-guiding device for a specified drilling resistance measurement unit that is configured to guide a specified drilling needle and configured to be operatively coupled with a drive of the drilling resistance measurement unit, the needle-guiding device comprising:
 a needle holder comprising a drill chuck configured to receive the specified drilling needle;
 a support device arranged in front of the needle holder and extending in a longitudinal direction of the specified drilling needle, the support device comprising at least one scissor-type extension arm device comprising a first scissor-type extension arm comprised of first stays;
 wherein the at least one scissor-type extension arm device comprises a second scissor-type extension arm comprised of second stays, wherein the first and second scissor-type extension arms each have an extended state and each define a plane in the extended state, wherein the planes are parallel to each other, wherein the first stays of the first scissor-type extension arm are arranged such that two of the first stays crossing each other, respectively, are connected to each other pivotably by a first joint, wherein the second stays of the second scissor-type extension arm are arranged such that two of the second stays crossing each other, respectively, are connected to each other pivotably by a second joint, wherein the first and second joints are connected to each other by a support structure, respectively, wherein the support structures each comprise a passage as a receptacle for the specified drilling needle, and wherein the passages of all of the support structures are positioned between the first and second scissor-type extension arms and are aligned with each other and with an opening of the needle holder.

11. A drilling resistance measurement unit for investigating the nature of wood, the drilling resistance measurement unit comprising a needle-guiding device according to claim 10.

12. The drilling resistance measuring unit according to claim 11, the drilling resistance measurement unit comprising a feed drive that is configured to transfer the first scissor-type extension arm from a folded state into an extended state.

13. A needle-guiding device for a specified drilling resistance measurement unit that is configured to guide a specified drilling needle and configured to be operatively coupled with a drive of the drilling resistance measurement unit, the needle-guiding device comprising:
 a needle holder comprising a drill chuck configured to receive the specified drilling needle;
 a support device extending in a longitudinal direction of the specified drilling needle, the support device embodied as a drive device comprising a first interacting force transmitting element and a second interacting force transmitting element arranged parallel adjacent to each other, wherein the needle holder is attached to the drive device and configured to be moved by the drive device;
 wherein the drive device further comprises first and second tensioning pinions and first and second drive pinions, wherein the first and second drive pinions are configured to be driven by a feed drive of the specified drilling resistance measurement unit, wherein the first interacting force transmitting element comprises a first end guided about the first tensioning pinion and comprises a second end guided about the first drive pinion, and wherein the second interacting force transmitting element comprises a first end guided about the second tensioning pinion and comprises a second end guided about the second drive pinion, wherein the needle holder is attached to the drive device and transferable by the drive device from a rear position, in which the needle holder is positioned at a proximal end of the drive device adjacent to the drilling resistance measurement unit, into a forward position in which the needle holder is positioned at a remote end of the drive device remote from the drilling resistance measurement unit, and wherein the first interacting force transmitting element comprises a first guide element and the second interacting force transmitting element comprises a second guide element that is in operative connection with the first guide element, wherein the first and second guide elements form an enclosure for the specified drilling needle.

14. A drilling resistance measurement unit for investigating the nature of wood, the drilling resistance measurement unit comprising a needle-guiding device according to claim 13.

15. A needle-guiding device for a specified drilling resistance measurement unit that is configured to guide a specified drilling needle and configured to be operatively coupled with a drive of the drilling resistance measurement unit, the needle-guiding device comprising:
- a needle holder comprising a drill chuck configured to receive the specified drilling needle;
- a support device extending in a longitudinal direction of the specified drilling needle, the support device embodied as a drive device comprising a first interacting force transmitting element and a second interacting force transmitting element arranged parallel adjacent to each other, wherein the needle holder is attached to the drive device and configured to be moved by the drive device;
- wherein the first and second interacting force transmitting elements are two chains each comprising chain members comprising bolts and links, wherein an enclosure for the specified drilling needle is formed by the bolts of the chain members, wherein the bolts comprise an inward curvature corresponding to an outer shape of the drilling needle, wherein the two chains extend adjacent to each other such that the links of one of the two chains mesh with the links of the other of the two chains.

16. A drilling resistance measurement unit for investigating the nature of wood, the drilling resistance measurement unit comprising a needle-guiding device according to claim 15.

17. A needle-guiding device for a specified drilling resistance measurement unit that is configured to guide a specified drilling needle and configured to be operatively coupled with a drive of the drilling resistance measurement unit, the needle-guiding device comprising:
- a needle holder comprising a drill chuck configured to receive the specified drilling needle;
- a support device extending in a longitudinal direction of the specified drilling needle, the support device embodied as a drive device comprising a first interacting force transmitting element and a second interacting force transmitting element arranged parallel adjacent to each other, wherein the needle holder is attached to the drive device and configured to be moved by the drive device;
- wherein the first and second interacting force transmitting elements are two toothed belts each comprising hooks at a toothless side of the two toothed belts, respectively, wherein the hooks of one of the two toothed belts engages the hooks of the other of the two toothed belts in an engagement position, wherein the hooks each comprise a cutout and in the engagement position the cutouts overlap each other and provide a round passage as an enclosure for the specified drilling needle.

18. A drilling resistance measurement unit for investigating the nature of wood, the drilling resistance measurement unit comprising a needle-guiding device according to claim 17.

* * * * *